United States Patent [19]
Lloyd et al.

[11] Patent Number: 6,077,222
[45] Date of Patent: Jun. 20, 2000

[54] METHOD AND DEVICE FOR DETECTING EDEMA

[75] Inventors: Lester John Lloyd, Orinda; Jorah Wyer, Mountain View, both of Calif.

[73] Assignee: Alere Incorporated, San Francisco, Calif.

[21] Appl. No.: 08/958,688

[22] Filed: Oct. 28, 1997

[51] Int. Cl.[7] ........................................................ A61B 5/00
[52] U.S. Cl. ................................................................ 600/300
[58] Field of Search .................................... 600/300, 587, 600/59; 128/898, 897

[56] References Cited

U.S. PATENT DOCUMENTS

| | | |
|---|---|---|
| 3,791,375 | 2/1974 | Pfeiffer . |
| 3,890,958 | 6/1975 | Fister et al. . |
| 3,974,491 | 8/1976 | Sipe ........................................ 340/272 |
| 4,144,749 | 3/1979 | Whitmore ................................ 73/149 |
| 4,383,533 | 5/1983 | Bhagat et al. . |
| 4,838,275 | 6/1989 | Lee . |
| 5,052,405 | 10/1991 | Batchelder . |
| 5,323,650 | 6/1994 | Fullen et al. ............................. 73/172 |
| 5,385,069 | 1/1995 | Johnson, Jr. ............................. 73/571 |

OTHER PUBLICATIONS

Boland, R. et al., "Development and Evaluation of a Precision Forearm and Hand Volumeter and Measuring Cylinder," *J. Hand Ther* (1996) vol. 9, No. 4:349–358.

Breytenbach, H.S., "Objective Measurement of Post–Operative Swelling," *Int. J. Oral Surg.* (1978) vol. 7:386–392.

Dramaix, M. et al., "Serum Albumin Concentration, Arm Circumference, and Oedema and Subsequent Risk Of Dying In Children In Central Africa," *BMJ* (1993) vol. 307:710–713.

Lindah, O.A., et al., "Impression Technique for the Assessment of Oedema: Comparison With A New Tactile Sensor That Measures Physical Properties Of Tissue," *Med. & Biol. Eng. & Comput.*, (1995) vol. 33:27–32.

Miyazaki, S., et al., "Foot–Force Measuring Device For Clinical Assessment of Pathological Gait," *Med. & Biol. Eng. & Comput.* (1978) vol. 16:429–436.

Mridha, M. et al., "Fluid Translocation Measurement," *Scand j Rehab Med* (1989) vol. 21:63–69.

Mridha, M., et al., "Noninvasive Method For The Assessment of Subcutaneous Oedema," *Medical & Biological Engineering & Computing* (1986) vol. 24:393–398.

Starr, Thomas W., "A Computerized Device for the Volumetric Analysis of the Residual Limbs of Amputess," *Bulletin of Prosthetics Research BPR* 10–33 (1980) vol. 17, No. 1,:98–102.

Swedborg, Iwona, "Voluminmetric Estimation of the Degree of Lymphedema and its Therapy By Pneumatic Compression," *Scand J Rehab Med* (1977) vol. 9:131–135.

*Primary Examiner*—Samuel Gilbert
*Attorney, Agent, or Firm*—Paula A. Borden; Bozicevic, Field & Francis LLP

[57] ABSTRACT

Methods and devices are provided for detecting the presence of edema in a mammalian host. In the subject methods, at least one limbic extremity of the host, preferably a lower limbic extremity such as an ankle or foot, is introduced into a container of a displaceable medium to result in displacement of a portion of the medium. The displaced portion is measured and the measured value is then compared to a control value to identify any difference. The difference is then related to the presence of edema in the patient. The subject methods find use in the diagnosis and management of diseases characterized by the presence of edema as a physical manifestation, particularly congestive heart failure.

21 Claims, 2 Drawing Sheets

METHOD AND DEVICE FOR DETECTING EDEMA

TECHNICAL FIELD

The field of this invention is diseases characterized by edema.

BACKGROUND OF THE INVENTION

Edema is defined as the abnormal accumulation of fluid in connective tissue. Edema typically results from a combination of passive venous congestion and salt and water retention, and may be systemic or localized to a particular region of the body. Dependent edema, in which fluid accumulates in the tissues of the limbic extremities, e.g. ankle, foot and the like, is a physical manifestation of a number of different human disease conditions. Dependent edema first appears in the feet and ankles of the ambulatory patient, and in the posterior surface of the calves and skin overlying the sacrum in the bedridden patient. Disease conditions characterized by the presence of dependent edema include local venous or lymphatic obstruction, cirrhosis, hypoalbumenia, and congestive heart failure.

In congestive heart failure, the presence of edema in the lower extremities is a valuable diagnostic marker for the presence of the disease. In addition to serving as a marker for the presence of congestive heart failure, the progression of the edemic state can be monitored over time and the progression of the edemic state related to the progression of the disease.

One way of detecting the presence of edema is to determine fluid volume change of the patient. A number of different technologies have been developed to identify the volume change, and include those based on the use of water or air-filled cuffs, mercury strain gauge, fiber optic strain gauge, and airborne ultrasound. Such technologies have principally been employed to measure venous blood flow and to sense the volume pulsations created by the heart.

Another way of detecting the presence of edema is the "pitting" method. In this method, a physician's thumb or finger is pressed into the patient's skin next to a bony surface (e.g., tibia, fibula, or sacrum). When the physician's finger is withdrawn, an indentation persists for a short time. The depth of the "pit" is estimated and generally recorded in millimeters, although subjective grading systems (e.g. "+++" etc.) have also been described. In general, the distribution of edema is also noted, as the amount of fluid is roughly proportional to the extent and the thickness of the pit.

Because dependent edema is a physical manifestation of a number of different disease conditions, the development of accurate methods for the detection of edema is of interest. Of particular interest is the development of methods which are sufficiently inexpensive and simple so as to be amenable to use in both conventional and out-patient health-care settings.

Relevant Literature

Scientific American Medicine (Dale & Freeman eds)1:I provides a review of congestive heart failure, physical manifestations and methods for the treatment thereof.

Lindahl & Omata, Med. Biol. Eng. Comput. (1995) 33:27–32 provide a description of methods of assessing edema.

Other references of note include U.S. Pat. Nos.: 3,791,375; 3,890,958; 3,974,491; 4,144,749; 4,383,533; 5,052,405; 5,323,650; and 5,385,069; as well as Swedborg, Scand. J. Rehab. Med. (1977) 9:131–135; Mridha & Ödman, Scand. J. Rehab. Med. (1989)21:63–39; Mridha & Ödman, Med. Biol. Eng. Comput. (1986) 24: 393–398; Kushner et al., Am. J. Clin. Nut. (1986) 44: 417–424; Breytenbach, Int. J. Oral Surg. (1978) 7:386–392; Davies et al., Med. Biol. Eng. Comput. (1971) 9:567–570; Lindhal et al., Med. Biol. Eng. Comput. (1991) 29: 591–597; Iwakura, Med. Biol. Eng. Comput. (1978) 16:429–436; and Starr, BPR (1980) 17:98–102.

SUMMARY OF THE INVENTION

Methods and devices for detecting the presence of and/or monitoring edema are provided. In the subject methods, a lower extremity of a host is introduced into a container comprising a displaceable medium, resulting in the displacement of a portion of the displaceable medium. The amount of the displaced portion is then determined and related to the volume of the lower extremity introduced into the container. From the measured volume, the presence or absence of edema is determined. The measurement may be repeated a number of times, so that the progression of the edemic state can be monitored. The subject methods find use in the diagnosis and management of a number of different diseases where edema is a physical manifestation, including local venous or lymphatic obstruction, cirrhosis, hypoalbuminemia and congestive heart failure.

DESCRIPTION OF THE SPECIFIC EMBODIMENTS

Figure 1A:
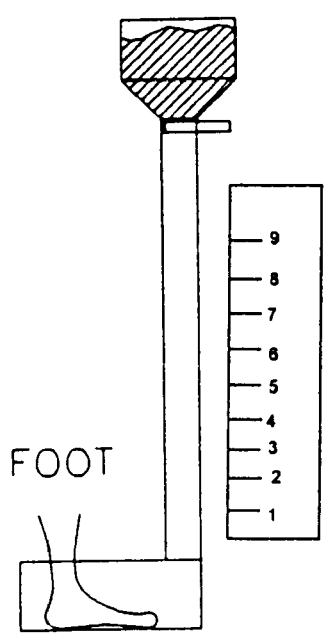
FIGS. 1a to 1c provide a depiction of a first embodiment of the method according to the subject invention in which the displaceable medium is a particulate composition or "macro-fluid."

Methods and devices are provided for monitoring edema. In the subject methods, at least one limbic extremity (preferably an ankle or foot) of a mammalian host is introduced into a container of a displaceable medium resulting in displacement of a portion of the medium. The displaced medium is measured and the measured value is then related to the presence or absence of edema. In the subject methods, the measurement may be made a plurality of times, usually according to a predetermined schedule, so that the progression of the edemic state may be monitored. The subject methods find use in the diagnosis and management of diseases characterized by the presence of edema, particularly congestive heart failure.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

The first step of the subject methods is to introduce at least one lower extremity into a container having present therein a volume of a displaceable medium. A variety of mediums may be employed as the displaceable medium. Suitable mediums include: (a) liquid mediums, such as aqueous compositions, e.g. water, other physiologically acceptable aqueous fluids, mineral oil, and the like; (b) gaseous mediums, e.g. air, nitrogen, carbon dioxide, and the like; and (c) particulate or "macro-fluid" compositions, such as compositions of round beads or other particulate like structures, where the particulate like structures will have an average diameter ranging from about 0.02 to 0.50 in, usually 0.05 to 0.50 in and more usually 0.05 to 0.40 in, and will be fabricated from any suitable material, such as plastic beads, ceramic beads, glass spheres, or naturally occurring bead like materials, such as dried beans, e.g. kidney and pinto, and the like, where macrofluids are preferred in many situations for their ease of use and reduced mess.

The nature of the container into which the extremity is introduced will necessarily depend on the particular displaceable medium present therein. Where liquid displaceable mediums are employed, the container may be as simple as a box shaped container having a circular, rectangular, square, irregular or other convenient cross-sectional configuration and open at the top so as to be capable of receiving the extremity into the interior thereof. Conveniently, such a container may have a scale present on one or more sides thereof to facilitate the rapid determination of the displaced fluid volume, as described in greater detail below. Alternatively, a more complicated configuration may be employed where a gaseous medium is employed as the displaceable medium. In such instances, the container will generally be a sealable container so that upon introduction of the extremity into the container, an increase in pressure of the gaseous medium results. Exemplary containers are further described in terms of the figures below.

Introduction of the extremity of the host into the container results in displacement of a portion of the displaceable medium. The next step in the subject method is therefore to measure or quantitate the amount of the medium which is displaced and to assign a value to this amount based on the measurement. Any convenient means of measuring the amount of displaced medium may be employed, where the specific methodology employed will necessarily depend on the specific nature of the medium. Thus, where the displaceable medium is a liquid, the amount of displaced medium can readily be measured by using a container having a graduated scale, where the original volume value of the medium prior to introduction of the extremity is subtracted from the new value as measured with the extremity submerged in the liquid. In such embodiments, it is useful to have the graduated scale located on the container in a region of reduced cross-sectional area as compared to the region of the container housing the extremity, since the change in volume will be magnified in such a region and therefore easier to assess.

Where a "macro-fluid" or particulate composition is used as the medium, one can use a similar method where one has a container with a graduated scale. Thus, by using a container of constant volume and a constant amount or number of beads, one first obtains an initial value of the beads in the container without the extremity. Next, the beads are removed and the extremity is introduced into the container. The beads are then reintroduced and the original volume value is subtracted from the new volume value. The resultant difference is the amount of medium displaced is then related to the volume of the extremity. Alternatively, one has the opportunity to use a "counting" method in which the number of beads needed to fill the container is first determined, followed by removal of the beads and introduction of the extremity, followed by reintroduction of a sufficient number of beads to again fill the container. The difference in the number of beads needed to fill the container with and without the extremity present therein is then determined, where means of determining the difference include weighing the beads or counting the beads, e.g. with a bead flow sensor, and the difference is related to the amount of the medium displaced. Prior to each measurement, the macro-fluid may be agitated to ensure adequate packing of the material in the container.

Where a gaseous medium is employed, the gaseous medium will generally be present in a sealable container. The sealable container is one that is capable of receiving the extremity and forming a seal around the extremity to thereby trap the gaseous medium in the container around the extremity. A variety of container configurations may be employed, where suitable configurations will be those in which the extremity is inserted into an opening which then seals around the extremity. Representative structures are further discussed in terms of the figures below. A variety of gaseous mediums may be employed, as described above, where air is a preferred medium.

The amount of gaseous medium displaced upon introduction of the extremity into the sealable container may be measured a number of different ways and related to the volume of the foot. Typically, the amount of displaced medium will be measured indirectly by looking at changes in parameters related to the volume of the gaseous medium that is displaced, e.g. changes in volume of the container and changes in pressure in the container. Two convenient ways of measuring the amount of displaced gas are the variable pressure mode and the variable volume mode. In the variable pressure mode, The extremity, e.g. the foot, is sealed in the container and the internal pressure of the container is raised to a preselected value that is greater than atmospheric pressure. The volume of the container is then decreased by a preselected amount with a volume modulation means, e.g. a piston. The resultant increase in pressure is then recorded, and the recorded value is used to ultimately derive the volume of the extremity in the container. In the variable volume mode, the extremity is again sealed in the container and internal pressure of the container is raised to a preselected pressure that is greater than atmospheric pressure. A volume modulation means, e.g. a piston, is then used to decrease the volume of the container. When the pressure in the container exceeds the initial pressure by a preselected amount, the volume change is recorded and used to ultimately derive the volume of the extremity in the container.

In the subject methods, the next step is to compare the measured displaced media value to a control value. The control value will be a value which corresponds to the amount of media displaced by an at least analogous extremity in the absence of the edemic state. Where possible to measure the limb in the absence of edema, such as in the case of pregnancy or surgery when the measurement can be made at an early time in anticipation of later indications of edema, then such non-edemic measurements can be used as a control value. Most often this is not possible as the desirability of edemic measurements is not apparent until the edema is already a problem. In this case the best indication of the non-edemic control value is simply the lowest value obtained from a series measurements taken over a period of time. If a microprocessor or other computer device is available, then the recording and displaying of the measurements allows an instant graphic display of not only the measured amount of edema but, often more importantly, whether the condition is worsening or improving. The measured displaced media value and the control value will be compared and any difference will be identified.

The presence of a positive difference between the measured value and the control value is then correlated to the presence of swelling in the region of measurement and edema in the patient. Conversely, the absence of a difference or a negative difference may be related to the absence or improvement of the edemic state. Accordingly, the final step of the subject methods is to attribute the presence of a positive difference to the presence of edema in the patient.

The subject methods may be used to make multiple measurements over a given period of time so that the progression of the edemic state may be monitored. Where multiple measurements are made, the measurements will typically be made according to a schedule, where the measurements may be made hourly, daily, weekly, monthly and the like.

A microprocessor may be used in the conjunction with the subject methods. For example, the measured value may be input into a microprocessor device that then takes the data and performs the comparison with a predetermined control value and provides a readout of any difference. The microprocessor could also transmit the input data to a remote site for further processing and use. Such an embodiment finds use in applications where measurements are taken at sites remote to the medical personnel in charge of interpreting the results, such as in outpatient clinics, at the home and the like.

Figure 1B:
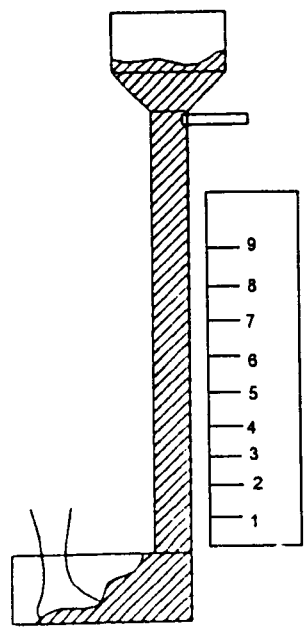
Figure 1C:
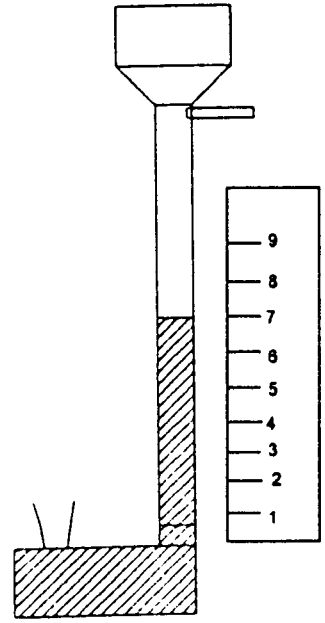

Turning now to the figures, FIGS. 1a to 1c depict a representative use of a macro fluid medium, e.g. beads, to determine the presence of edema according to the subject invention. A volume of beads is first introduced into an empty container and the level to which the beads reach in the column is recorded. The beads are then removed and a foot is introduced into the container, as shown in FIG. 1a. The beads are then reintroduced into the container as shown in FIG. 1b. The level to which the beads reach when the foot is present in the container, as shown in FIG. 1c, is then recorded. The difference in level values in the presence and absence of the foot in the container is then related to the volume of the foot. The scale is located in a region of reduced cross-section area in order to provide for easier reading of the amount of change, since the change is amplified in this region.

Figure 2:
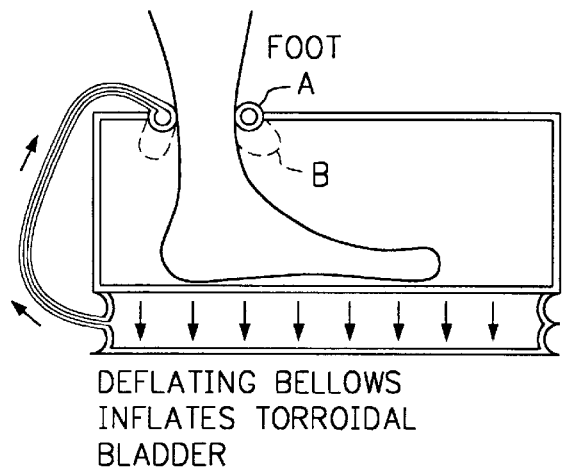
FIG. 2 provides a depiction of a second embodiment of the method according to the subject invention in which the displaceable medium is a gas.

In FIG. 2 is depicted an embodiment of the subject invention in which air is employed as the displaceable medium. In FIG. 2 the container comprises a bladder of air as the floor. When the foot is placed in the opening and onto the bladder, the bladder compresses resulting in inflation of a torrus shaped bladder around the ankle. The torroidal shaped bladder conforms to the ankle and seals a fixed mass of air around the foot inside the box. In some embodiments, the torroidal bladder will take all of the air from the lower chamber and expand from condition A to condition B. In other embodiments, the torroidal bladder may leak into the chamber and form a seal but not distend to the full volume of the lower chamber. The torroidal bladder may be fitted with apertures to permit gas to move into the chamber surround the foot so as to maintain sufficient pressure around the ankle to minimize leaking. The box can then be pressurized and depressurized as required, either through an additional aperture or through the torroidal bladder. Optionally, the torroidal bladder can be inflated with a mechanical pump.

Figure 3A:
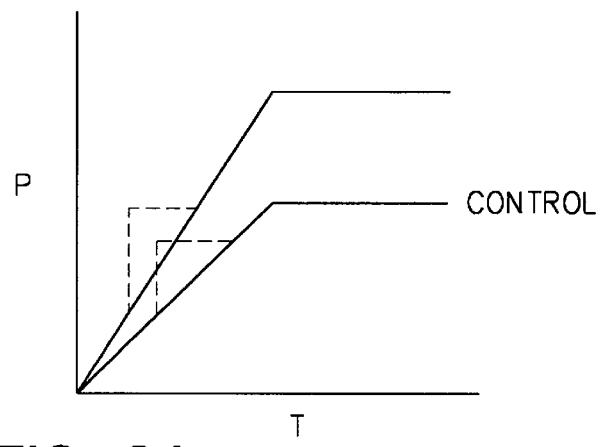
FIGS. 3a & 3b are graphs of the pressure vs. time derived from data obtained from a device as shown in FIG. 2.
Figure 3B:
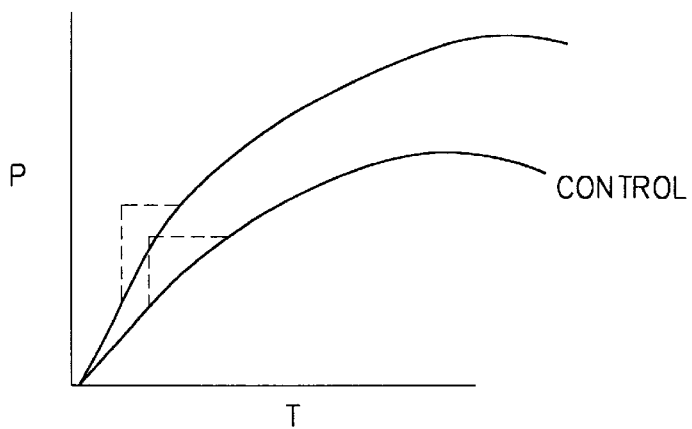

With this embodiment, air from the bladder can be used for both inflation of the cuff and pressurization of the container housing the extremity. The measurement of pressure can be made by either measuring the final pressure or measuring the pressure differential of the box over a given period of time, i.e. looking at the change in pressure over a given period of time. These methods can be used in situations where the cuff either makes a perfect seal or imperfectly seals the container such that there is a leakage of gaseous medium from the container. If a perfect seal is achieved, one can measure the pressure over a period of time and plot the results in a graph as shown in FIG. 3A. If an imperfect seal is achieved, the pressure over time can still be plotted to obtain a graph as shown in FIG. 3B. In either method, one can then derive slope values for a selected region of the line and compare these values to obtain measurements from which the edemic state of the extremity can be derived.

Alternatively, the foot could be placed into a container having a thin, airtight sock. An iris analogous to the aperture of a camera would then close around the top of the sock and the foot. Upon pressurization, the sock is forced tightly around the foot. The iris prevents parts of the sock from being pushed out the top of the box by the increased pressure.

The subject methods find use with a variety of mammalian hosts where the detection of dependent edema is desired. Mammalian hosts with which the subject methods may find use include highly valuable, rare and exotic animals, domestic animals, such as livestock and pets, and humans.

Of particular interest is the use of the subject methods in the diagnosis and management of human diseases in which dependent edema is a physical manifestation, such as venous or lymphatic blockage, cirrhosis, hyperalbumenia and congestive heart failure, where congestive heart failure is of particular interest.

In using the subject methods in the diagnosis of congestive heart failure, the detection of edema by the subject methods is used as an indication of the presence of congestive heart failure. In making such diagnoses, jugular venous distention may also be detected, since the presence of both conditions can be used as assurance that the underlying disease condition is congestive heart failure, and not another disease characterized by the presence of dependent edema, such as local venous or lymphatic obstruction, cirrhosis or hypoalbumenia.

Also of particular interest is the use of the subject methods in the management of congestive heart failure. In managing congestive heart failure, a plurality of measurements will be taken according to a schedule and the progression the edemic state will be monitored. In this manner, the affect of various treatment methodologies on the symptoms associated with and/or the progression of the underlying disease can be assessed.

The following examples are offered by way of illustration and not by way of limitation.

EXPERIMENTAL

A. A sixty-one year old man with congestive heart failure resides at home with a care giver. A computerized telephonic monitoring system is installed which transmits information to a centralized nursing station. The system requires the patient to complete a daily monitoring cycle which includes answering questions on his general health, appetite, and any unusual symptoms. As well, the patient stands on an electronic scale which records his weight, and while seated on a closed toilet seat or in a low chair places his foot on an indicated location in the device shown in FIG. 2. The patient presses a button to record the measurements and detaches the apparatus. At a later time, the computer system transmits the entire information set collected, including the edema measurements, to the central station. With an analysis of this daily information, a physician has early warning information, and can provide prompt care, avoiding acute episodes. Of particular interest is use of the subject methods and devices as part of the patient interface system disclosed in U.S. patent application Ser. No. 08/958,689 filed Oct. 28, 1997 entitled Patient Interface System and filed concurrently herewith, the disclosure of which is herein incorporated by reference.

It is evident from the above results and discussion that improved methods for detecting dependent edema in a mammalian host are provided. Because the subject methods use relatively simple and inexpensive measurement devices, they are amenable for use in high volume situations and out patient settings by moderately skilled personnel, and therefore provide an attractive alternative to currently employed methods of detecting edema which are based on the detection of volume changes.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for at least one of diagnosing and monitoring a congestive heart failure condition in a mammalian host, said method comprising:
    introducing an extremity of said host into a container comprising a displaceable medium whereby a portion of said displaceable medium is displaced;
    measuring said displaced medium, thereby obtaining a measured amount value;
    relating said measured amount value to the presence or absence of edema in said host; and
    relating said presence or absence of edema to said congestive heart failure condition.

2. The method according to claim 1, wherein said extremity is a lower extremity.

3. The method according to claim 2, wherein said lower extremity is selected from the group consisting of ankle and foot.

4. The method according to claim 1, wherein said relating step comprises comparing the measured amount value to a control value and attributing any difference in values to the presence or absence of edema.

5. The method according to claim 1, wherein said displaceable medium is a liquid.

6. The method according to claim 1, wherein said displaceable medium is a particulate composition.

7. The method according to claim 1, wherein said displaceable medium is a gas.

8. A method for at least one of diagnosing and monitoring a congestive heart failure condition in a human, said method comprising:
    introducing at least one lower extremity of said human into a container comprising a displaceable medium, whereby a portion of said medium is displaced;
    measuring said displaced medium, thereby obtaining a measured displaced medium value;
    comparing the measured displaced medium value to a control value to obtain a difference;
    attributing any difference to the presence or absence of edema in said human; and
    relating said presence or absence of edema to said congestive heart failure condition.

9. The method according to claim 8, wherein said lower extremity is selected from the group consisting of foot and ankle.

10. The method according to claim 8, wherein said displaceable medium is a liquid and said measuring step comprises determining a volume of liquid displaced upon introduction of said extremity into said container.

11. The method according to claim 8, wherein said displaceable medium is a particulate composition and said measuring step comprises quantifying an amount of said particulate composition that is displaced upon introduction of said extremity into said container.

12. The method according to claim 8, wherein said displaceable medium is a gas and said measuring step comprises quantifying an increase in pressure of said gas upon introduction of said extremity into said container.

13. The method according to claim 8, further comprising the step of inputting said measured displaced medium value into a microprocessor.

14. The method according to claim 8, further comprising the step of transmitting said measured displaced medium value to a site remote from the site where said value is measured.

15. The method according to claim 8, further comprising the steps of measuring said value a plurality of times and monitoring the progression of said edema.

16. A method for monitoring a congestive heart failure condition in a patient suffering from congestive heart failure, said method comprising:
    introducing a lower extremity of said patient into a container comprises a displaceable medium, whereby a portion of said medium is displaced;
    measuring the displaced medium, thereby obtaining a measured displaced medium value;
    comparing the measured displaced medium value of said lower extremity to a control value and determining any difference;
    attributing said difference to the presence or absence of edema in said patient; and
    relating said presence or absence of edema to said congestive heart failure condition.

17. The method according to claim 16, wherein said displaceable medium is a liquid and said measuring step comprises determining a volume of liquid displaced upon introduction of said extremity into said container.

18. The method according to claim 16, wherein said displaceable medium is a particulate composition and said measuring step comprises quantifying a amount of said particulate composition that is displaced upon introduction of said extremity into said container.

19. The method according to claim 16, wherein said displaceable medium is a gas and said measuring step comprises quantifying an increase in pressure of said gas upon introduction of said extremity into said container.

20. The method according to claim 16, further comprising the step of using said method in the diagnosis of said congestive heart failure.

21. The method according to claim 16, further comprising the step of using said method in the management of said congestive heart failure.

* * * * *